(12) United States Patent  
Bedor (10) Patent No.: US 8,409,259 B1
(45) Date of Patent: Apr. 2, 2013

(54) CERVICAL PLATE SYSTEM AND METHOD

(76) Inventor: Bernard M. Bedor, Daytona Beach, FL (US)

( * ) Notice: Subject to any disclaimer, the term of this patent is extended or adjusted under 35 U.S.C. 154(b) by 273 days.

(21) Appl. No.: 12/885,913

(22) Filed: Sep. 20, 2010

Related U.S. Application Data (63) Continuation-in-part of application No. 12/652,833, filed on Jan. 6, 2010.

(51) Int. Cl.
*A61B 17/80* (2006.01)

(52) U.S. Cl. ...................................... 606/289

(58) Field of Classification Search ........... 606/289–296
See application file for complete search history.

(56) References Cited

U.S. PATENT DOCUMENTS

| | | | |
|---|---|---|---|
| 4,493,317 A | 1/1985 | Klaue | |
| 5,578,034 A | 11/1996 | Estes | |
| 5,741,258 A | 4/1998 | Klaue et al. | |
| 5,931,838 A | 8/1999 | Vito | |
| 6,224,602 B1 | 5/2001 | Hayes | |
| 6,454,771 B1 | 9/2002 | Michelson | |
| 6,503,250 B2 | 1/2003 | Paul | |
| 6,602,255 B1 | 8/2003 | Campbell et al. | |
| 6,652,525 B1 | 11/2003 | Assaker et al. | |
| 6,695,846 B2 | 2/2004 | Richelsoph et al. | |
| 7,115,130 B2 | 10/2006 | Michelson | |
| 7,306,605 B2 | 12/2007 | Ross | |
| 7,438,715 B2 | 10/2008 | Doubler et al. | |
| 7,468,069 B2 | 12/2008 | Baynham et al. | |
| 7,625,381 B2 | 12/2009 | Michelson | |
| 7,736,380 B2 | 6/2010 | Johnston et al. | |
| 2003/0187440 A1 | 10/2003 | Richelsoph et al. | |
| 2004/0097950 A1 | 5/2004 | Foley et al. | |
| 2004/0236335 A1 | 11/2004 | Michelson | |
| 2005/0234455 A1 | 10/2005 | Binder et al. | |
| 2006/0100626 A1 | 5/2006 | Rathbun et al. | |
| 2006/0122603 A1 | 6/2006 | Kolb | |
| 2006/0200146 A1 | 9/2006 | Doubler et al. | |
| 2007/0043369 A1* | 2/2007 | Wallenstein et al. ........... 606/69 |
| 2007/0083203 A1 | 4/2007 | Ribeiro | |
| 2008/0287999 A1 | 11/2008 | Markworth | |
| 2009/0024170 A1 | 1/2009 | Kirschman | |
| 2009/0062863 A1 | 3/2009 | Peppers | |
| 2009/0182383 A1 | 7/2009 | Prybyla et al. | |
| 2009/0210010 A1 | 8/2009 | Strnad et al. | |
| 2009/0234393 A1 | 9/2009 | Sournac et al. | |
| 2010/0049256 A1 | 2/2010 | Jeon et al. | |

FOREIGN PATENT DOCUMENTS

WO 2008094572 A2 8/2008

* cited by examiner

*Primary Examiner* — Kevin T Truong
*Assistant Examiner* — Sameh Boles
(74) *Attorney, Agent, or Firm* — Roetzel & Andress; Jason S. Miller (57) ABSTRACT

A cervical plate system (1) and method for use in the fixation of a spine comprising a fixation plate (2) having an aperture (3) extending from a top surface (5) to a bottom surface (19) and dimensioned for admitting at least a portion of a bone fixation element (4) shank (15) therethrough, a slot (7) extending into the bottom surface (19), and a lock (11) affixed adjacent the fixation plate bottom surface (19) for rotation relative to the fixation plate (2).

7 Claims, 7 Drawing Sheets

CERVICAL PLATE SYSTEM AND METHOD

CROSS-REFERENCE TO RELATED APPLICATION

This application is a continuation-in-part of and claims priority to patent application Ser. No. 12/652,833, filed Jan. 6, 2010, entitled "Cervical Plate System and Method", the disclosure of which is incorporated by reference hereinto.

BACKGROUND OF THE INVENTION

1. Field of the Invention

The present invention relates to cervical plate systems and methods, more specifically, a cervical plate system that provides retention of a bone fixation element wherein vertical movement of the bone fixation element is significantly reduced.

2. Description of Related Art

Cervical spine surgery is a neurosurgical procedure for treating a wide variety of cervical spine disorders and deformities, including, but not limited to, cervical deformation, disc degeneration, arthritis, and congenital defects. In addition, cervical spine surgery is utilized to treat cervical fractures, injuries, or other traumas to the spine wherein the spine becomes displaced or otherwise altered from such fracture, injury, or trauma.

The procedure utilizes synthetic devices to anchor two or more vertebrae to one another in the spinal column. Such devices may include bone fixation elements, also referred to as bone screws, coupled to a fixation plate. The bone fixation elements are positioned within apertures located in the fixation plate are driven into the desired vertebrae. Such devices are typically temporary devices used to stabilize bone fragments or bones to one another until the fragments heal and/or the bones are fused to one another. As the ultimate goal of utilizing such synthetic devices is to limit movement of the cervical spine to promote healing, it is of great importance that fixation between the bone fixation element and fixation plate be secure.

Various structures for securing fixation plates to vertebrae are currently available wherein bone fixation elements are inserted through apertures located in the fixation plate and driven into the vertebrae. A problem associated with utilizing such bone fixation elements in cervical plate systems, however, is "backing out" wherein movement of the bone fixation element(s) occur. Such backing out may be in reference to movement of the bone fixation element in a vertical, horizontal, lateral, rotational, or any other direction of movement post-insertion of the bone fixation element into the bone.

To minimize such movement, various cervical plate systems include the use of locking plates wherein the locking plate is adjusted so as to cover the head of the bone fixation element once the bone fixation element has been inserted into the bone. In this manner, vertical movement of the bone fixation element is limited due to the head of the bone fixation element abutting the locking plate. Although use of a locking plate that covers the head of the bone fixation element prevents vertical backing out of the bone fixation element to a certain degree, vertical backing out is possible if there exists a distance between the top surface of the head of the bone fixation element and the bottom surface of the locking plate adjacent to the bone fixation element head. Moreover, locking plates that cover the head of the bone fixation element may not prevent or minimize backing out in other directions, such as horizontal, lateral, rotational, or other directional movement of the bone fixation element.

Thus there exists a need for an improved cervical plate system that minimizes movement of a bone fixation element after its insertion into the bone.

SUMMARY OF THE INVENTION

The present invention is directed to a cervical plate system comprising a fixation plate having an aperture extending from a first surface to a second surface opposed to the first surface thereof. The aperture is dimensioned for admitting at least a portion of a shank of a bone fixation element therethrough, and for preventing the head from passing therethrough, and a slot extending into the second surface.

A lock may be affixed adjacent the fixation plate second surface for rotation relative to the fixation plate between a first position adapted for permitting relative axial movement of the bone fixation element and a second position adapted for substantially preventing axial movement of the bone fixation element.

Additional embodiments of the cervical plate system of the present invention include the lock located upon slideable plates.

The present invention is also directed to a method for fixating a spine comprising positioning a fixation plate adjacent to a bone in a spine; inserting a bone fixation element into an aperture of the fixation plate such that a portion of the bone fixation element is located within the aperture and is adjacent to the bone; driving the bone fixation element into the bone such that at least a portion of a shank of the bone fixation element extends through the aperture and into the bone; and rotating the lock from a first position wherein the lock disengages at least a portion of the bone fixation element to a second position wherein the lock engages at least a portion of the bone fixation element.

Additional methods for fixating a spine of the present invention include the lock located thereupon.

DETAILED DESCRIPTION OF THE PREFERRED EMBODIMENTS

A description of the preferred embodiments of the present invention will now be presented.

Figure 1:
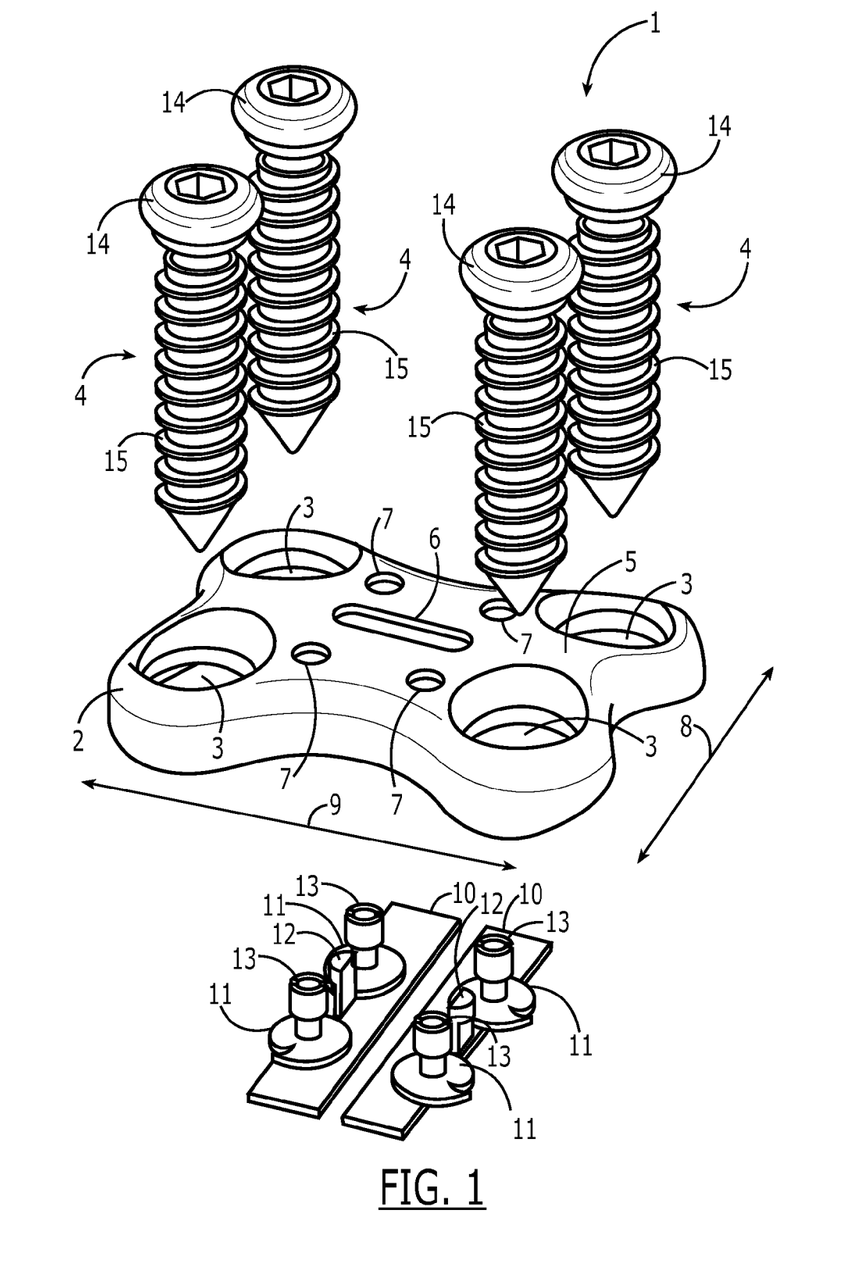
FIG. 1 is an isometric exploded view of a cervical plate system of the present invention.

With reference to FIG. 1, an isometric exploded view of a cervical plate system of the present invention is shown. The cervical plate system 1 includes a fixation plate 2 having at least one aperture 3 for insertion of at least one bone fixation element 4, here, four, therethrough. The fixation plate 2 has a top surface 5 and may include at least one fixation plate slot 6 and at least one locking plate slot 7. The fixation plate slot 6 may be sized and shaped to permit a user to manipulate a lock 11 between engaged and disengaged positions as described below. The bone fixation element 4 may comprise an element such as a bone screw, screw, or any other type of fastening means.

The bone fixation elements 4 extend through the apertures 3 of the fixation plate 2. When located within the apertures 3, a head 14 of the bone fixation element 4 is located in line with or below the top surface 5 of the fixation plate 2 while a shank portion 15 of the bone fixation element 4 extends downwardly for ultimate insertion into a bone.

The cervical plate system 1 may also include at least one locking plate 10 that is slidingly adjustable along a lateral axis 8 or a longitudinal axis 9 (as shown) of the fixation plate 2. At least one lock 11 is positioned on the locking plate 10. The lock 11 includes a vertically extending lock protrusion 13, which is sized so as permit a least a portion of the lock protrusion 13 to extend through the locking plate slot 7 in the fixation plate 2.

When the locking plate 10 is in a disengaged position, a sufficient amount of the aperture 3 is unrestricted to permit at least a portion of the shank 15 of a bone fixation element 4 to extend therethrough. When the locking plate 10 is in an engaged position, the bone fixation retaining means 11 engages at least a portion of the bone fixation element 4; that is, the bone fixation retaining means 11 abuts at least a portion of the head 14 and/or shank 15 of the bone fixation element 4.

The locking plate 10 may be located adjacent a bottom surface 19 of the fixation plate 2; however, the locking plate 10 may be located adjacent the top surface 5 of the fixation plate 2, or between the top surface 5 and the bottom surface 19.

The locking plates 10 may also include at least one locking plate protrusion 12 sized and shaped for movement within the fixation plate slot 6 in the fixation plate 2.

Figure 2:
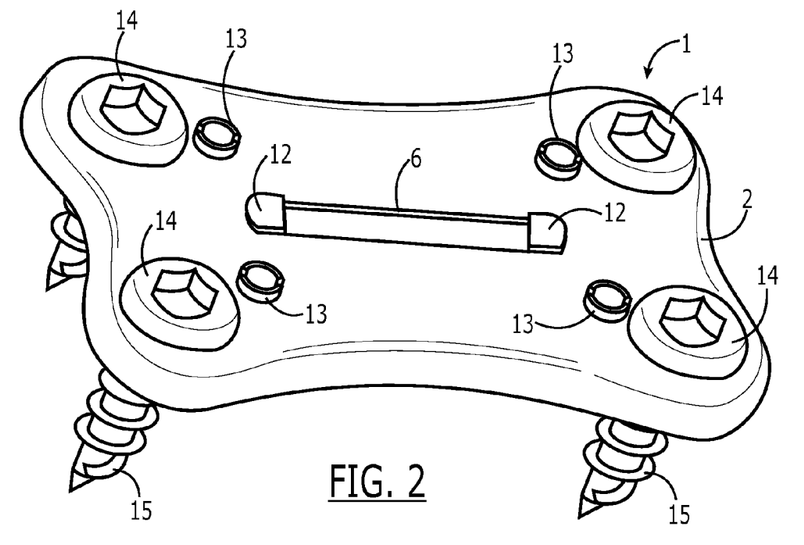
FIG. 2 is a perspective top view of the cervical plate system of the present invention.

FIG. 2 shows a perspective top view of the cervical plate system of the present invention. When assembled, the locking plate protrusions 12 on the locking plates 10 are moveable within the fixation plate slots 6 of the fixation plate 2. Additionally, once the locking plates 10 are positioned as desired, the lock 11 may be rotated (or torqued) so as to engage the bone fixation elements 4 against or within the bone fixation retaining means 11 so as to minimize movement of the bone fixation elements 4.

Figure 3:
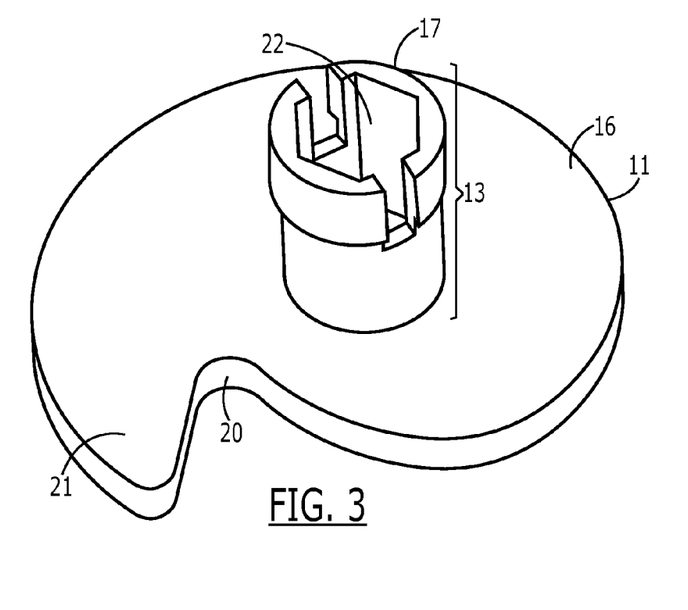
FIG. 3 is a perspective top view of a lock of the present invention.
Figure 4:
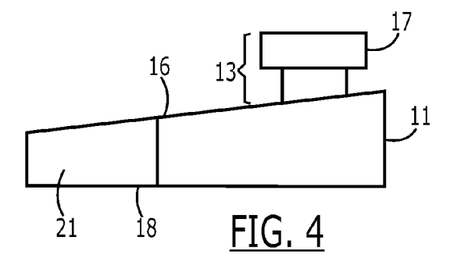
FIG. 4 is a side view of the embodiment of FIG. 3.

FIGS. 3 and 4 show varying views of the lock 11 of the present invention. The lock 11 includes a top surface 16 and a bottom surface 18. The lock also includes a lock protrusion 13 that substantially vertically extends from the top surface 16 of the lock 11. A lock protrusion head 17 is preferably located atop the lock 13, which may include a rotating means 22 to permit an end user to easily torque or rotate the bone fixation element receiving means 11 via use of an allen wrench or other device. In the alternative, the head 17 may sized and shaped so as to permit an end user to easily manually or electronically torque or rotate the lock 11.

As shown in this figure, the lock 11 is substantially round in shape and includes a notch 20 and an arm 21. When the lock 11 is rotated, at least a portion of the bone fixation element 4 may be positioned within the notch 21. In such position, movement of the bone fixation element 4 is minimized. In the alternative, when the lock 11 is rotated, at least a portion of the bone fixation element 4 may be positioned adjacent to the lock 11, and not necessarily positioned within the notch 21. In such position, because a predetermined amount of pressure is applied to the bone fixation element 4, movement of the bone fixation element is minimized. The lock 11 may include a gradual incline or ramp, which, when the lock 11 is rotated, provides an additional means for securing the lock 11 on or about the bone fixation element 4. However, inclusion of the incline on the lock 11 is not required. The lock 11 may be press fit within the locking plate slot 7 upon initial assembly of the present invention or upon receipt of the invention by an end user.

To use the cervical plate system 1 of the present invention to fixate a spine, a user first positions the fixation plate 2 adjacent to a bone in a spine. Then, the user inserts a bone fixation element 4 into an aperture 3 located in the fixation plate 2 such that a portion of the bone fixation element 4 is located within the aperture 3 and is adjacent to the bone. Next, the user drives the bone fixation element 4 into the bone such that at least a portion of the shank 15 extends through the aperture 3 and into the bone. The user then slides the locking plate 10 along the axis 8 or 9 from the disengaged position to the engaged position wherein the lock 11 engages at least a portion of the bone fixation element 4. The user may then further secure the bone fixation element 4 within the fixation plate 2 by rotating the lock 11 such that either the lock 11 abuts a least a portion of the bone fixation element 4 or the lock 11 at least partially circumscribes the bone fixation element 4.

Figure 5:
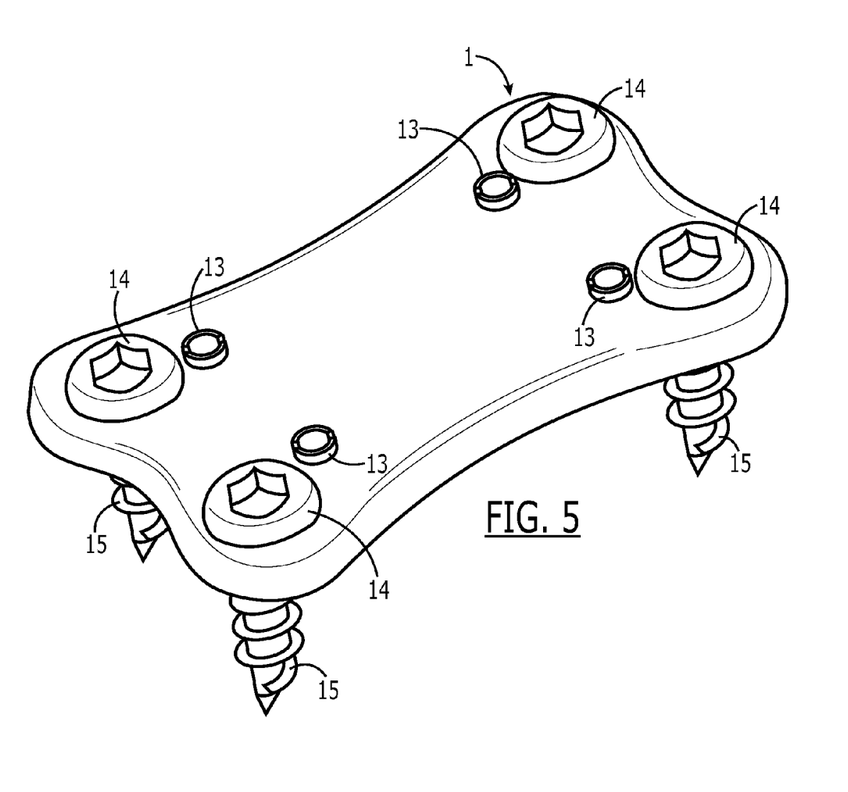
FIG. 5 is a perspective top view of an alternate embodiment of the cervical plate system of the present invention.
Figure 6:
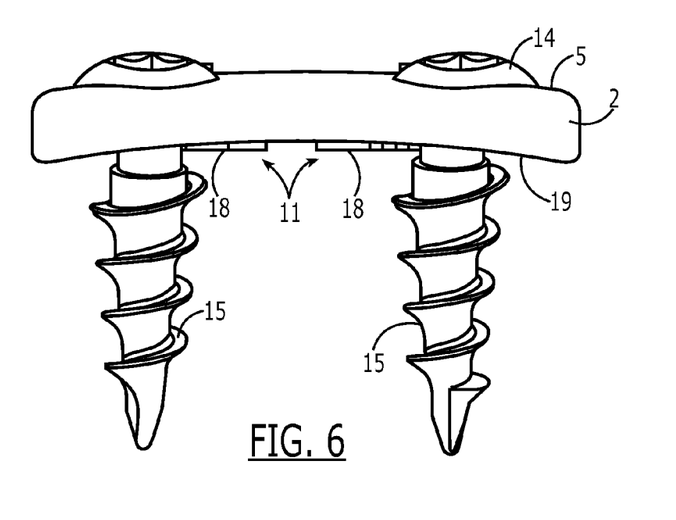
FIG. 6 is a side view of the embodiment of FIG. 5.
Figure 7:
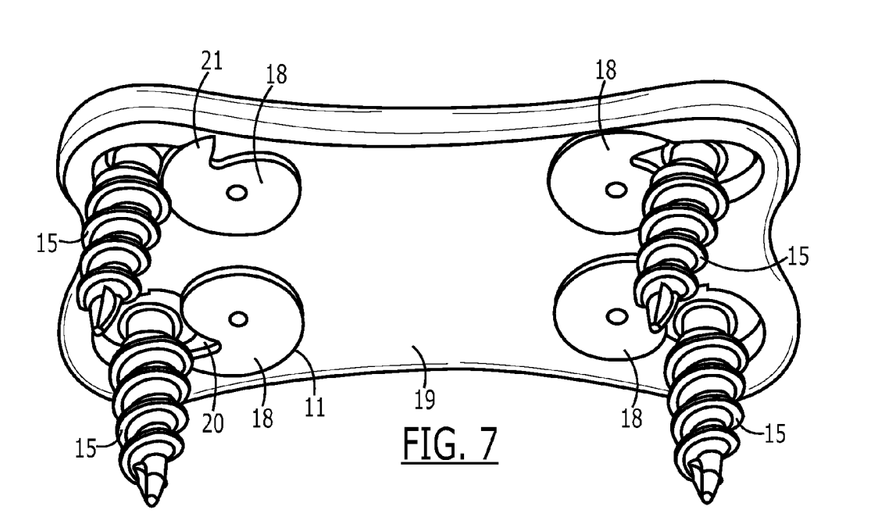
FIG. 7 is perspective bottom view of the embodiment of FIG. 5.

With reference to FIGS. 5-7, varying views of an alternate embodiment of the cervical plate system of the present invention are shown. Similar to the previously described embodiment of the present invention, the cervical plate system 1 includes a fixation plate 2 having at least one aperture 3 for insertion of at least one bone fixation element 4 therethrough. The fixation plate 2 has a top surface 5 and at least one locking plate slot 7. The fixation plate slot 6 may be sized and shaped to permit a user to manipulate a lock 11 between engaged and disengaged positions as described below. The bone fixation element 4 may be a bone screw, screw, or any other type of fastening means.

The bone fixation elements 4 extend through the apertures 3 of the fixation plate 2. When located within the apertures 3, a head 14 of the bone fixation element 4 is located in line with or below the top surface 5 of the fixation plate 2 while a shank portion 15 of the bone fixation element 4 extends downwardly for ultimate insertion into a bone.

When the lock 11 is in a disengaged position, a sufficient amount of the aperture 3 is unrestricted to permit at least a portion of the shank 15 of a bone fixation element 4 to extend therethrough. When the lock 11 is in an engaged position, the bone fixation retaining means 11 engages at least a portion of the bone fixation element 4; that is, the bone fixation retaining means 11 abuts at least a portion of the head 14 and/or shank 15 of the bone fixation element 4.

To use the cervical plate system 1 of the present invention to fixate a spine as depicted in FIG. 5, a user first positions the fixation plate 2 adjacent to a bone in a spine. Then, the user inserts a bone fixation element 4 into an aperture 3 located in the fixation plate 2 such that a portion of the bone fixation element 4 is located within the aperture 3 and is adjacent to the bone. Next, the user drives the bone fixation element 4 into the bone such that at least a portion of the shank 15 extends through the aperture 3 and into the bone. The user then secures the bone fixation element 4 within the fixation plate 2 by rotating the lock 11 such that either the lock 11 abuts a least a portion of the bone fixation element 4 or the lock 11 at least partially circumscribes the bone fixation element 4.

Figure 8:
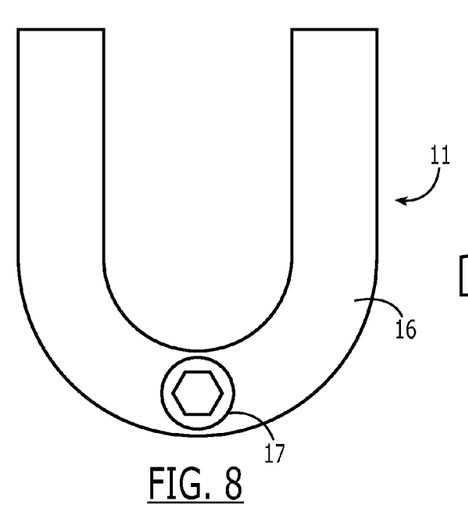
FIG. 8 is a top view of an alternate embodiment of a lock of the present invention.
Figure 9:
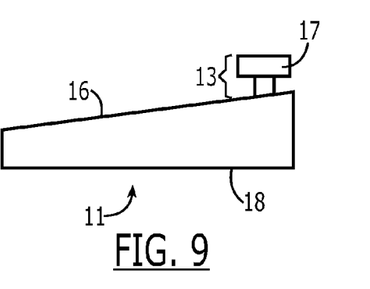
FIG. 9 is a side view of the embodiment of FIG. 8.

FIGS. 8 and 9 show varying views of the lock 11 of the present invention. The lock 11 includes a top surface 16 and a bottom surface 18. The lock also includes a lock extension 13 that substantially vertically extends from the top surface 16 of the lock 11. A lock protrusion head 17 is preferably located atop the lock 13, which may include a rotating means 22 to permit an end user to easily rotate the bone fixation element receiving means 11 via use of an allen wrench or other device. In the alternative, the head 17 may sized and shaped so as to permit an end user to easily manually or electronically rotate the lock 11.

As shown in this figure, the lock 11 is substantially U-shaped. When the lock 11 is rotated, at least a portion of the bone fixation element 4 may be positioned within the U-shaped configuration. In such position, movement of the bone fixation element 4 is minimized. In the alternative, when the lock 11 is rotated, at least a portion of the bone fixation element 4 may be positioned adjacent to the lock 11, and not necessarily positioned within lock 11. In such position, because a predetermined amount of pressure is applied to the bone fixation element 4, movement of the bone fixation element is minimized. The lock 11 may include a gradual incline or ramp, which, when the lock 11 is rotated, provides an additional means for securing the lock 11 on or about the bone fixation element 4. However, inclusion of the incline on the lock 11 is not required. The lock 11 may be press fit within the locking plate slot 7 upon initial assembly of the present invention or upon receipt of the invention by an end user.

Figure 10:
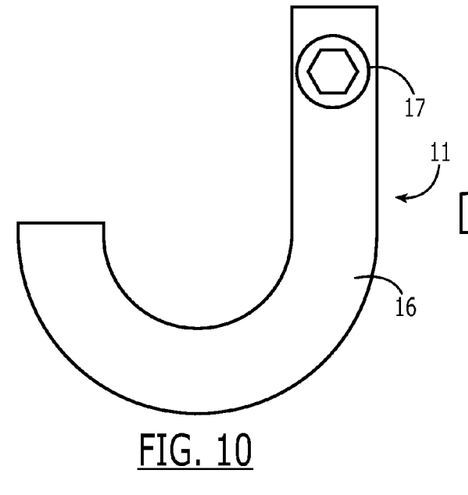
FIG. 10 is a top view of an alternate embodiment of a lock of the present invention.
Figure 11:
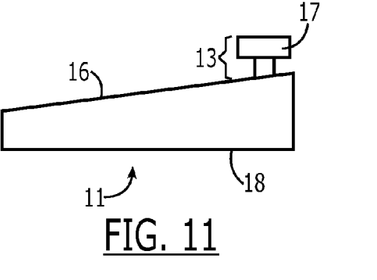
FIG. 11 is a side view of the embodiment of FIG. 10.

FIGS. 10 and 11 show varying views of the lock 11 of the present invention. The lock 11 includes a top surface 16 and a bottom surface 18. The lock also includes a lock extension 13 that substantially vertically extends from the top surface 16 of the lock 11. A lock protrusion head 17 is preferably located atop the lock 13, which may include a rotating means 22 to permit an end user to easily rotate the bone fixation element receiving means 11 via use of an allen wrench or other device. In the alternative, the head 17 may sized and shaped so as to permit an end user to easily manually or electronically rotate the lock 11.

As shown in this figure, the lock 11 is substantially hook-shaped. When the lock 11 is rotated, at least a portion of the bone fixation element 4 may be positioned within the hook-shaped configuration. In such position, movement of the bone fixation element 4 is minimized. In the alternative, when the lock 11 is rotated, at least a portion of the bone fixation element 4 may be positioned adjacent to the lock 11, and not necessarily positioned within lock 11. In such position, because a predetermined amount of pressure is applied to the bone fixation element 4, movement of the bone fixation element is minimized. The lock 11 may include a gradual incline or ramp, which, when the lock 11 is rotated, provides an additional means for securing the lock 11 on or about the bone fixation element 4. However, inclusion of the incline on the lock 11 is not required. The lock 11 may be press fit within the locking plate slot 7 upon initial assembly of the present invention or upon receipt of the invention by an end user.

Although various shapes of the lock 11 are shown, such is a non-exclusive depiction of the various shapes which may be utilized for the lock 11.

Figure 12:
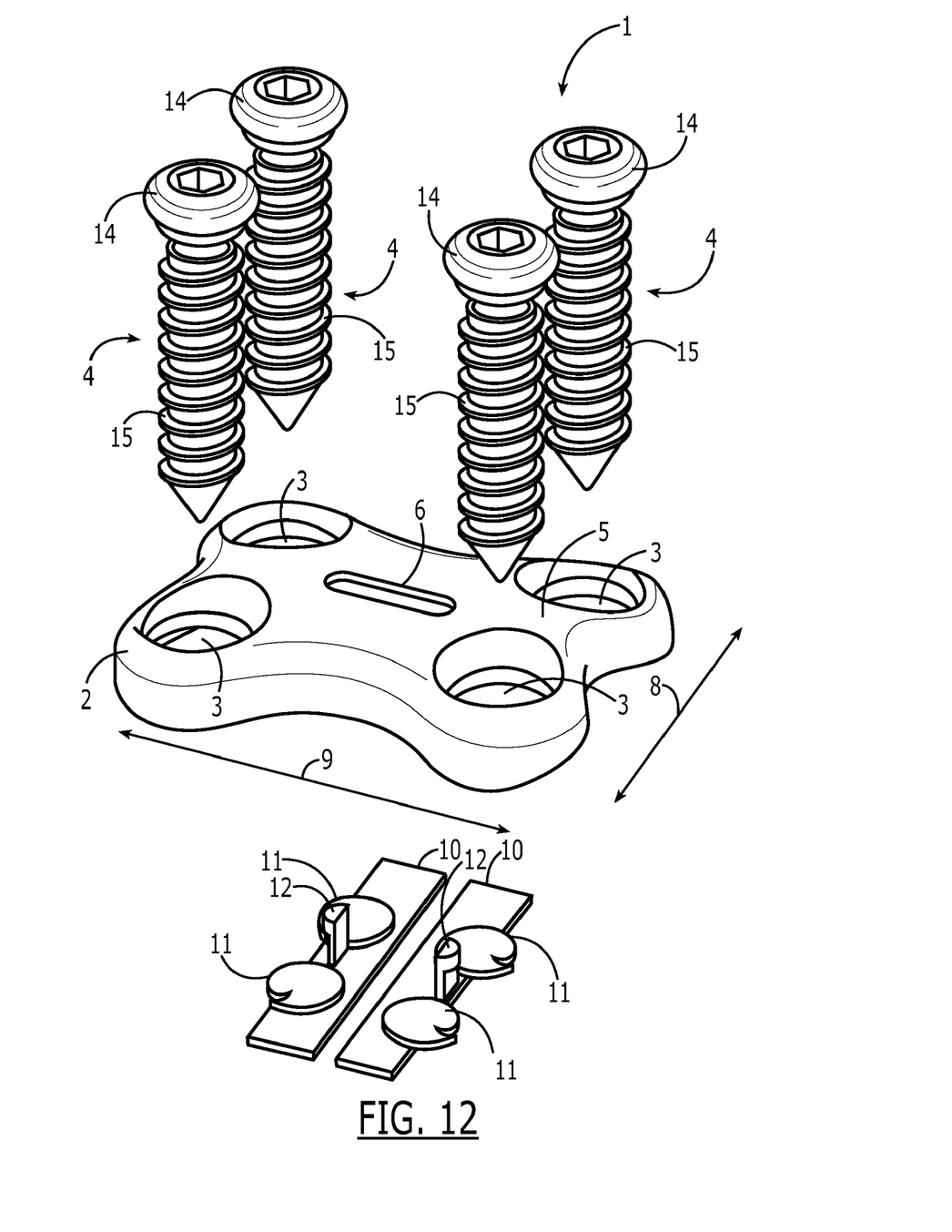
FIG. 12 is an isometric exploded view of an alternate embodiment of the cervical plate system of the present invention.

With reference to FIG. 12, an isometric exploded view of another embodiment of the cervical plate system of the present invention is shown. The fixation plate 2 has an aperture 3 extending from a top surface 5 to a bottom surface 19 and dimensioned for admitting at least a portion of a shank portion 15 of a bone fixation element 4 therethrough. In this manner, the head 14 of the bone fixation element 4 is also prevented from passing through the aperture 3. A fixation plate slot 6 extends into the bottom surface.

A locking plate 10 has a top surface 16 and a bottom surface 18 and is adapted for outward sliding movement relative to the fixation plate 2. The locking plate 10 has a recess 23 along an outer edge 24 of the locking plate 10. The locking plate 10 is movable between a first position to permit an end user to insert a bone fixation element 4 through the fixation plate 2 aperture 3, and a second position wherein the recess 23 engages the bone fixation element shank 15. In this second position, axial movement of the bone fixation element 4 is substantially prevented. The locking plate 10 also includes a locking plate protrusion 12 extending from the top surface 16 and dimensioned for registering with the fixation plate slot 6 during sliding of the locking plate 10 between the first and the second position. The locking plate 10 has a recess that, as shown in this figure, is substantially round in shape. When the locking plate 10 is slid, at least a portion of the bone fixation element 4 may be positioned within the recess 23. In such position, movement of the bone fixation element 4 is minimized.

Figure 13:
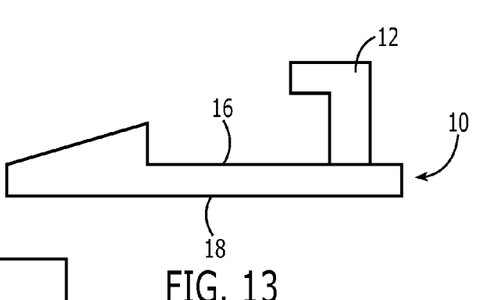
FIG. 13 is a side view of the embodiment of FIG. 12.

FIG. 13 shows a side view of the locking plate of the embodiment of FIG. 12. The locking plate 10 may include a gradual incline or ramp, which, when the locking plate 10 is slid, provides an additional means for securing the locking plate 10 on or about the bone fixation element 4.

To use the cervical plate system 1 of the present invention to fixate a spine, a user first positions the fixation plate 2 adjacent to a bone in a spine. Then, the user inserts a bone fixation element 4 into an aperture 3 located in the fixation plate 2 such that a portion of the bone fixation element 4 is located within the aperture 3 and is adjacent to the bone. Next, the user drives the bone fixation element 4 into the bone such that at least a portion of the shank 15 extends through the aperture 3 and into the bone. The user then slides the locking plate 10 along the axis 8 or 9 from the disengaged position to the engaged position wherein the recess 23 engages at least a portion of the bone fixation element 4.

Figure 14:
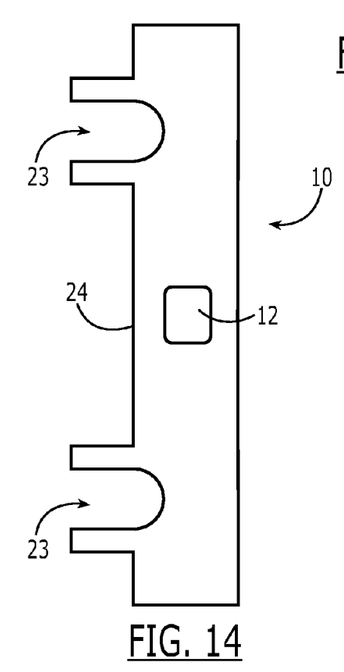
FIG. 14 is a top view of an alternate embodiment of a locking plate of the present invention.
Figure 15:
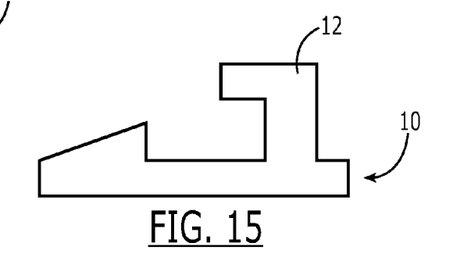
FIG. 15 is a side view of the embodiment of FIG. 14.

FIGS. 14 and 15 show varying views of the recess 23 of the present invention. The recess 23 includes a top surface 16 and a bottom surface 18. As shown in this figure, the recess 23 is substantially U-shaped. When the locking plate 10 is slid, at least a portion of the bone fixation element 4 may be positioned within or against the U-shaped configuration. In such position, because a predetermined amount of pressure is applied to the bone fixation element 4, movement of the bone fixation element is minimized. The recess 23 may include a gradual incline or ramp, which, when the locking plate 10 is slid, provides an additional means for securing the recess 23 on or about the bone fixation element 4.

Figure 16:
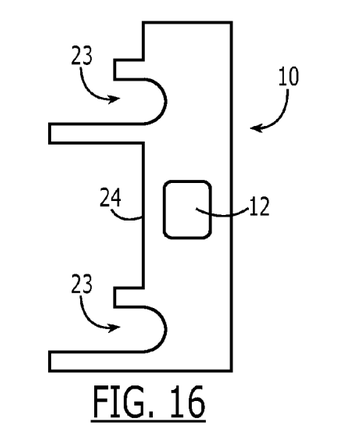
FIG. 16 is a top view of an alternate embodiment of a locking plate of the present invention.
Figure 17:
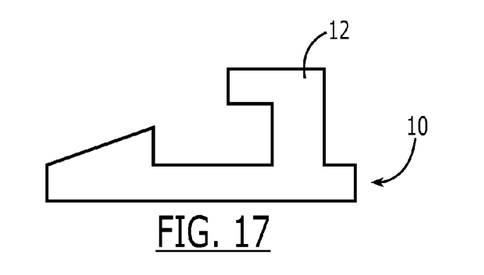
FIG. 17 is a side view of the embodiment of FIG. 16.

Finally, FIGS. 16 and 17 show varying views of the recess 23 of the present invention. The recess 23 includes a top surface 16 and a bottom surface 18. As shown in this figure, the recess 23 is substantially hook-shaped. When the locking plate 10 is slid, at least a portion of the bone fixation element 4 may be positioned within or against the hook-shaped configuration. In such position, because a predetermined amount of pressure is applied to the bone fixation element 4, movement of the bone fixation element is minimized. The recess 23 may include a gradual incline or ramp, which, when the locking plate 10 is slid, provides an additional means for securing the recess 23 on or about the bone fixation element 4.

Although various shapes of the recess 23 are shown, such is a non-exclusive depiction of the various shapes which may be utilized for the recess 23.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A cervical plate system comprising: a fixation plate having: an aperture extending from a first surface to a second surface opposed to the first surface thereof and dimensioned for admitting at least a portion of a shank of a bone fixation element therethrough, and for preventing the head from passing therethrough; and a slot extending into the second surface; and a locking plate having a first surface and a second surface opposed to the first surface, the locking plate adapted for sliding movement along longitudinal axis of the fixation plate relative to the second surface, the locking plate first surface adjacent the fixation plate second surface, the locking plate comprising a lock rotatably affixed to the locking plate second surface and engageable with the bone fixation element, the lock movable between a first position adapted for permitting relative axial movement of the bone fixation element and a second position adapted for substantially preventing axial movement of the bone fixation element, the locking plate further having a protrusion extending from the first surface and dimensioned for registering with the fixation plate slot during sliding of the locking plate between the first and the second position; the lock has a protrusion extending toward the second surface, and the fixation plate further has a hole extending therethrough from the first surface to the second surface, the hole dimensioned for admitting at least a portion of the lock protrusion thereinto and for permitting relative rotation therebetween.

2. The cervical plate system of claim 1, wherein the fixation plate second surface comprises a bottom surface.

3. The cervical plate system of claim 1, wherein the fixation plate second surface comprises a top surface.

4. The cervical plate system of claim 1, wherein the locking plate is slidingly secured to the fixation plate at a location between the fixation plate first surface and the fixation plate bottom surface.

5. The cervical plate system of claim 1, wherein the lock at least partially circumscribes the bone fixation element shank when the locking plate is in the second position.

6. The cervical plate system of claim 1, wherein the lock has a notch adapted for admitting the bone fixation element shank thereinto when the locking plate is in the second position.

7. The cervical plate system of claim 1, wherein at least a portion of a first surface of the lock adjacent the fixation plate second surface has an incline.

* * * * *